United States Patent [19]
Rodan et al.

[11] Patent Number: 5,461,034
[45] Date of Patent: Oct. 24, 1995

[54] OSTEOGENIC GROWTH POLYPEPTIDES IDENTIFIED FROM REGENERATING BONE MARROW

[75] Inventors: Gideon A. Rodan, Bryn Mawr, Pa.; John W. Jacobs, Irvine, Calif.; Mohinder K. Sardana, Lansdale, Pa.; Dan Gazit, Jerusalem, Israel; Michael Chorev, Jerusalem, Israel; Andras Muhlrad, Jerusalem, Italy; Arye Shteyer, Jerusalem, Israel; Nura Mansur, Jerusalem, Israel; Zvi Greenberg, Jerusalem, Israel; Shimon Slavin, Jerusalem, Israel; Olga Gurevitch, Jerusalem, Israel; Itai A. Bab, Jerusalem, Israel

[73] Assignee: Yissum Research Development Company of the Hebrew University of Jerusalem, Jerusalem, Israel

[21] Appl. No.: 79,637

[22] Filed: Jun. 18, 1993

Related U.S. Application Data

[63] Continuation-in-part of Ser. No. 809,214, Dec. 16, 1991, abandoned, which is a continuation of Ser. No. 734,018, Jul. 22, 1991, abandoned, which is a continuation of Ser. No. 639,307, Jan. 19, 1991, abandoned, which is a continuation of Ser. No. 544,074, Jun. 25, 1990, abandoned, which is a continuation of Ser. No. 314,602, Feb. 23, 1989, abandoned.

[51] Int. Cl.$^6$ .................. A61K 38/08; A61K 38/39; A61K 35/32; A61F 2/02
[52] U.S. Cl. .................. 514/14; 514/12; 514/21; 530/327; 530/350; 530/353; 530/355; 530/356; 530/397; 530/398; 530/399; 530/414; 530/416; 530/417; 530/840; 530/841; 930/10
[58] Field of Search .................. 424/95, 423; 514/12, 514/14, 21; 530/327, 350, 353, 355, 356, 414, 416, 417, 840, 841, 397, 398, 399; 930/10

[56] References Cited

U.S. PATENT DOCUMENTS

| 4,434,094 | 2/1991 | Seyedin et al. | 424/95 |
| 4,455,256 | 6/1984 | Urist | 530/350 |

FOREIGN PATENT DOCUMENTS

| 0241578 | 10/1987 | European Pat. Off. . |
| 0349048 | 1/1990 | European Pat. Off. . |

OTHER PUBLICATIONS

Chemical Abstracts, 31470b, vol. 76, No. 7 (Feb. 14, 1972).
Chemical Abstracts, 11400j, vol. 74, No. 1 (Jan. 4, 1971).
Bab et al., Calcified Tissue International 37, 551–555 (1985).
Taylor, J. Mol. Biol. 188, 233–254 (1986).
Kayne et al., Cell 55, 27–39 (1988).
Bab et al., Endocrinology 123, 345–352 (1988).
Wu et al., "Sequence and Organization of Histon gene clusters in Sea Stars", submitted to the EMBL Data Library, Jul. 1990, ref#: S20677.
Calas et al., "Solid–Phase Synthesis Using a New Polyacrylic Resin Synthesis of the Fragment 14–21 of the Amino–acid sequence of Histone H4", Tetrahedron 41 (22), 1985: 5331–5339.
Wefes et al., "The Two Macronuclear Histone H4 Genes of the Hypotrichous Ciliate Stylonychi Lemnae", DNA Sequence (1990) 1: 25–32.

(List continued on next page.)

Primary Examiner—Thurman K. Page
Assistant Examiner—Carlos Azpuru
Attorney, Agent, or Firm—William S. Frommer

[57] ABSTRACT

A biochemically pure polypeptide(s), termed osteogenic growth polypeptide (OGP), which exhibits stimulatory effects on osteoblastic cells, in vivo bone formation and hemopoietic reconstruction. OGP, identified from regenerating bone marrow, has an amino acid sequence of Ala-Leu-Lys-Arg-Gln-Gly-Arg-Thr-Leu-Tyr-Gly-Phe-Gly-Gly.

19 Claims, 4 Drawing Sheets

OTHER PUBLICATIONS

Harper et al., "Actin Tubulin and H4 Histone Genes in Three Species of Hypotrichous Ciliated Protozoa", Gene (1989) 75: 93–107.

Kremer et al., "Isolation and Characterization of a Drosophila Hydei Histone DNA Repeat Unit", Nucleic Acids Res. (1990) 18: 1573–1580.

Gazit et al., J. Bone Min. Res., 1:101 (1986).

Gazit et al., J. Bone, 7:389 (1986).

Gazit et al., J. Dent. Res., 66:909 (1987).

Huang et al., J. Oral Max. Surg., 46:460 (1988).

Shteyer et al., Mar. 9–13, 1988 Conference, Quebec, Canada.

Gazit et al., Connect. Tissue Res., 23:153 (1989).

Scheven et al., Bone Miner., 14:221–235 (Sep. 1991).

Dickson et al., Biochem. Biophys. Rec. Comm. 159:1383–1389 (Mar. 1989).

*P=0.019(Mann-Whitney)

FIG.3b

C57 BL♀ MICE

OSTEOGENIC GROWTH POLYPEPTIDES IDENTIFIED FROM REGENERATING BONE MARROW

CROSS-REFERENCE TO RELATED APPLICATIONS

This application is a continuation-in-part of application Ser. No. 07/809,214 filed Dec. 16, 1991, now abandoned, which is a continuation of application Ser. No. 07/734,018 filed Jul. 22, 1991, now abandoned, which is a continuation of application Ser. No. 07/639,307 filed Jan. 4, 1991, now abandoned, which is a continuation of application Ser. No. 07/544,074 filed Jun. 25, 1990, now abandoned, which in turn is a continuation of application Ser. No. 07/314,602 filed Feb. 23, 1989, now abandoned.

BACKGROUND OF THE INVENTION

It is well known that after marrow ablation there is an osteogenic phase where trabeculae of primary bone replace the blood clot and fill the marrow space. The trabeculae are then subjected to osteoclastic resorption that precedes the appearance of regenerated normal marrow. Not only is there osteogenic reaction locally in the marrow cavity, there is stimulation of bone formation in cortical osteons and enhancement of osteo- and chondrogenesis in distant skeletal sites. Observations in mandibular condyles during the osteogenic phase of postablation healing of tibial marrow suggested that the enhanced osteogenesis resulted from an increase in both the number and activity of osteoblasts. It has been proposed that a factor or factors are produced locally by the regenerating marrow that mediate the peripheral osteogenic response after their release into the blood circulation. Bab I. et al., (1988) Endocrinology 123:345; Bab. I. et al., (1985) Calcif Tissue Int 37:551.

The present invention establishes that regenerating bone marrow produces growth factor activity with an effect on osteogenic cells. Additionally, the present invention provides a novel osteogenic growth polypeptide, identified from regenerating bone marrow, which (i) has a stimulatory effect on osteoblastic cells, and (ii) promotes in vivo bone formation.

The novel osteogenic growth polypeptide of the present invention has sequence homology with histone H4, a 102 amino acid protein, and with a fragment of histone H4. Kayne P. S. et al., (1988) Cell 55:27–39; Kharchenho E. P., et al., (1987) Biull. Eksp. Biol. Med. 103(4): 418–420. The references, however, do not disclose polypeptides within the scope of the present invention and do not disclose any of the biological properties of the polypeptides of present invention.

Bone marrow transplantation (BMT) is progressively and rapidly becoming the treatment of choice in instances of hematological malignancies such as lymphomas, Hodgkins's disease and acute leukemia as well as solid cancers, in particular melanoma and breast cancer. Potentially, with improved methods, BMT can also be used for treating other catastrophic diseases—AIDS, aplastic anemia and autoimmune disorders. The aim of all BMT is to replace the host hemopoietic stem cells, totipotent and pluripotent, injured by chemotherapy, radiation or disease. These stem cells can replicate repeatedly and differentiate to give rise to the whole variety of cells present in blood-erythrocytes, platelets and white blood cells which include lymphocytes, monocytes and neutrophils. Resident macrophages and osteoclasts are also derived from hemopoietic totipotent stem cells. As the stem cells differentiate, they commit themselves more and more to a particular lineage until they can form only one kind of the above cells.

The most common way currently available for acquiring enough stem cells for transplantation is to extract one liter or more of marrow tissue from multiple sites in the donor's bones with needle and syringe, an involved process that usually requires general anesthesia. The donors of allogeneic BMT are usually siblings whose tissue types are compatible and sometimes unrelated donors who are matched to the recipient by HLA typing. Autologous transplants, that eliminate the need for HLA matching, may be used in patients undergoing ablative chemoradiotherapy for the eradication of solid tumors. Autologous stem cells may also be obtained from the umbilical cord blood at birth and stored for future administration.

After transplantation and prior to the establishment of a donor-derived functioning marrow the patients hosting BMT present with a transient marked pancytopenia that exposes them to infections. The incidence of bacterial and fungal infection correlates with both the severity and duration of pancytopenia [Slavin S. and Nagler A., (1992) Transplantation]. The recipient must therefore receive a steady supply of fresh red cells, platelets and antibiotics for several weeks until the transplanted stem cells begin producing large quantities of mature blood elements. In instances of allogenic BMT the recipient immune system must be sufficiently suppressed so that it will not reject the transplanted stem cells. At the same time, the transplanted donor's immune system may give rise to graft versus host disease (GVHD) and cause lethal tissue and organ damage. All these considerations dictate prolonged and expensive hospitalization.

BMT would be much more effective if a way could be found to accelerate the process of engraftment, enhance marrow reconstruction, reduce the medical hurdles and shorten the hospitalization period and the incidence of infection, morbidity and mortality [Gabrilove J. L., et al. (1988) N. Engl. J. Med. 318:1414]. The currently available clinical (experimental) treatment for stimulating post BMT marrow reconstruction consists mainly of the administration of recombinant human granulocyte colony stimulating factor (rhG-CSF) and/or recombinant human granulocyte-macrophage colony stimulating factor (rhGM-CSF) [Blazar R. B., et al. (1989) Blood 74:2264]. These cytokines affect directly the proliferation of transplanted pluripotent cells already committed to the white-cell lineages [Vellenga E., et al. (1987) Leukemia 1:584] and consequently decrease the time to leukocyte and neutrophil recovery.

There are, however, some major concerns regarding the therapeutic use of rhG-CSF and rhGM-CSF. Tumors and leukemic cells possess normal receptors for these cytokines [Vellenga E., et al. (1987) Leukemia 1:584] and their administration can increase relapse rates by enhancing the proliferation of residual host tumor cells. Another concern about using CSFs in the setting of BMT is that the CSFs, by stimulating the proliferation of relatively committed cells with no capacity for self renewal, deplete progenitor cell number [Slavin S. and Nagler A., (1992) Transplantation]. For a similar reason, the CSFs fail to support erythropoiesis and platelet formation.

Polypeptides that support hemopoiesis may prove useful in other ways as well. Some investigators have found that adding stem cells from the peripheral blood to those from the bone marrow significantly increases the rate of engraftment. Extracting sufficient numbers of stem cells from peripheral blood is a complicated procedure. Administering such polypeptides to donors to increase the number of stem cells in the blood will improve the feasibility of transplanting stem cells from peripheral blood [Gold D. W., (1991) Sci. Am., December:36].

A prerequisite for hemopoiesis and therefore successful BMT is the presence of functional stromal cells and tissue that comprise the hemopoietic microenvironment, determine the homing of the injected stem cells from the circulation to the bone marrow and support hemopoiesis [Watson J. D. and McKenna J. J., (1992) Int. J. Cell Cloning 10:144]. Marrow derived stromal tissue also provide the conditions to sustain stem cells in in vitro long-term bone marrow cultures. At present this technology suffices to keep stem cells alive. Adding the appropriate hemopoietic polypeptides to these cultures may help expand the stem cell population in vitro, thus providing increased numbers of these cells for transplantation. The combined in vitro-in vivo approach may provide the basis for a forward-looking strategy for (i) obtaining small stem cell preparations from donors' blood or marrow and (ii) healthy individuals to have their stem cells stored for a time when the cells might be needed to treat a serious disease, thus bypassing the complexity associated with the use of allogeneic BMT.

It would therefore be of therapeutic importance to find small peptides that stimulate post BMT hemopoietic reconstruction by enhancing in vivo and/or in vitro the hemopoietic microenvironment of which fibrous tissue, bone and bone cells are important components. Such peptides may also support hemopoiesis in spontaneous occurring or induced myelosuppression conditions that do not necessarily involve BMT.

Preablation therapy using molecules with an OGP-like activity is likely to enhance the hemopoietic microenvironment and consequently stimulate hemopoiesis at the non-committed stem cell level avoiding the stem cell depiction and white cell discrimination.

SUMMARY OF THE INVENTION

The present invention provides a newly isolated biochemically pure polypeptide (or polypeptides) (i) having a stimulatory effect on osteoblastic cells, and (ii) which promotes in vivo bone formation. This polypeptide was identified from regenerating bone marrow. The invention also provides a method of isolating the polypeptide from regenerating bone marrow, and a method of using the polypeptide to increase bone formation. The novel polypeptides of the present invention are also useful in pharmaceutical compositions, as screening tools and in the prevention, prophylaxis, therapy and treatment of diseases involving bone defects, bone loss and decreased bone formation, or other conditions which would benefit from increased bone formation. The novel polypeptides of the present invention are also useful in pharmaceutical compositions and in the therapy and treatment of conditions requiring the stimulation of hemopoietic reconstruction.

DESCRIPTION OF THE DRAWINGS

FIG. 3 shows a dose dependent effect of pretreatment with OGP(1–14) on the total number of femoral marrow cells in mice after combined ablative radiotherapy/BMT. sOGP at the indicated dose was injected subcutaneously daily for 12 days to female C57 Black mice. On day 8 after the onset of sOGP treatment the mice were subjected to 900 Rad X-ray irradiation followed by intravenous administration of $10^5$ syngeneic unselected marrow cells. On day fourteen after the onset of treatment the mice were sacrificed and the femoral marrow washed out into phosphate buffered saline. A single cell suspension was prepared by drawing the preparation several times through graded needles. Cell counts were carried out in a hemocytometer. C-control mice given phosphate buffered saline only. Data are mean±SEM obtained in at least seven mice per condition.

DETAILED DESCRIPTION OF THE INVENTION

Osteogenic growth polypeptide ("OGP") is a biochemically pure polypeptide identified from regenerating bone marrow and having a stimulatory effect on osteoblastic cells and in vivo bone formation. OGP, as used herein, is defined to include native polypeptides, synthetic polypeptides, all homologs, isoforms or genetic variants, and all other variants. The molecular weight of OGP is in the range of about 500 to 2600, preferentially of about 1000 to 1600, and more preferentially of about 1525.

OGP was purified to three different stages, from regenerating (or healing) bone marrow conditioned media (HBMCM), Stages 1 and 2A having partial purity, and Stage 2B having apparent homogenity.

The invention identifies as an effective stimulator of bone formation a 14-residue polypeptide. The native OGP was isolated and purified to homogeneity from culture media conditioned by osteogenic tissue obtained from rat tibiae during post-ablation marrow regeneration (HBMCM). The purification procedure consisted of chromatography and selection of chromatographic fractions showing biological activity, including size exclusion, heparin-Sepharose, ion-exchange and reverse-phase chromatography.

Following demonstration of its mitogenic activity, the purified polypeptide OGP was subjected to automated Edman degradation for amino acid sequence analysis. A synthetic polypeptide of identical sequence was prepared by solid-phase peptide synthesis. The synthetic polypeptide OGP (sOGP) was tested and found to have a stimulatory effect on osteoblastic cells. When injected intravenously daily to adult rats of about 200–250 g, sOGP promoted bone formation (measured as mineral apposition rate) at doses of from about 1 pg/rat/day to about 1 µg/rat/day.

The data suggests that OGP is a single polypeptide of identified sequence, however, the possibility of homologs, isoforms or genetic variants of OGP exists either within or outside the cellular environment. This invention encompasses all such homologs, isoforms or genetic variants of OGP, provided each has an effect on osteoblastic cells and on in vivo bone formation. Polypeptides that are homologs of OGP specifically include those having an amino acid sequence which is at least about 40% conserved in relation to the amino acid sequence set forth in Table A, preferentially at least about 60% conserved, and more preferentially at least about 75% conserved.

It will be understood by one or ordinary skill in the art that other variants of OGP are included within the scope of the present invention. This particularly includes any variants that differ from the isolated or synthesized OGP only by conservative amino acid substitution. Many such conservative amino acid substitutions are set forth as sets in Taylor, W. R., J. Mol. Biol. 188, 233 (1986). OGP, or fragments thereof, in this application includes any such variations in the amino acid sequence, whether by conservative amino acid substitution, deletion, or other processes, provided that the polypeptide after purification shows a stimulatory effect on osteoblastic cells and on in vivo bone formation. The fragments of OGP may be small peptides with sequences of as little as 6 or more amino acids, said sequences being those disclosed in Table A.

Polypeptides larger than OGP are also included within the scope of the present invention when said polypeptides have a stimulatory effect on osteoblastic cells and in vivo bone formation, and include a partial amino acid sequence as set forth in Table A, or conservative substitutions thereof.

The amino acid sequence of OGP is as follows:

Table A

Ala-Leu-Lys-Arg-Gln-Gly-Arg-Thr-Leu-Tyr-Gly-Phe-Gly-Gly

The amino acid sequence of OGP(2-14) is as follows:

Leu-Lys-Arg-Gln-Gly-Arg-Thr-Leu-Tyr-Gly-Phe-Gly-Gly.

The amino acid sequence of OGP(3-14) is as follows:

Lys-Arg-Gln-Gly-Arg-Thr-Leu-Tyr-Gly-Phe-Gly-Gly.

The amino acid sequence of OGP(4-14) is as follows:

Arg-Gln-Gly-Arg-Thr-Leu-Tyr-Gly-Phe-Gly-Gly.

The amino acid sequence of OGP(5-14) is as follows:

Gln-Gly-Arg-Thr-Leu-Tyr-Gly-Phe-Gly-Gly.

It will be readily apparent to one of ordinary skill in the art that a great deal of use can be made of the amino acid sequence of OGP. For example, oligonucleotide probes can be constructed from the amino acid sequence and employed to screen for the cDNA clones encoding OGP. These clones containing OGP cDNA(s) can be used to transcribe mRNA which can then be translated and expressed. This work with OGP can be used to produce large quantities of OGP by genetic engineering or to study the genetics of OGP to learn its cellular role in bone formation.

Additionally, synthetic polypeptides can be made in order to improve upon the pharmacological properties of OGP. These synthetic peptides can be made by the technique of solid-phase peptide synthesis developed by Merrifield ("Solid-Phase Peptide Synthesis", Advances in Enzymology, 32:221–296, 1969); G. Barnay & R. B. Merrifield "Solid-Phase Peptide Synthesis", The Peptides, Vol. 2, ed. E. Gross & J. Merenhole (1980). This method is based on the strategy of having the carboxyl terminus of the peptide linked covalently to a solid support. The desired peptide sequence is prepared by stepwise coupling of single amino acids to a peptide chain growing from the carboxyl toward the amino terminus. Coupling is typically achieved by activation of the carboxyl group of the amino acid being attached to the resin which may have other potentially reactive groups blocked. Following addition of amino acid to the growing polypeptide chain, and prior to further chain elongation, a protecting group is typically removed. Because each amino acid is coupled by nearly the same series of reactions, the need for elaborate strategies in the synthesis is minimized. Solubility is not a major issue during synthesis, because the peptide is linked to a solid support. This method is rapid and it can be utilized simply. It is very convenient for the synthesis of multiple analogs with amino-terminal substitutions, because a single synthesis can be branched in multiple directions near the amino terminus, thereby creating many analogs varying only in the amino terminal region.

Additionally, the amino acid sequence can be used to make polypeptides which can be used as a screen or tool for the identification of non-peptidal molecules which show a stimulatory effect on osteoblastic cells and in vivo bone formation.

The polypeptides of the present invention also find utility for the stimulation of bone formation, in instances of osteoporosis (or osteopenia of any etiology), fracture repair, healing of osseous defects or wounds, intraosseous implants, and bone supplementation, or other conditions requiring increased bone formation.

The polypeptides of the present invention also find utility for the stimulation of hemopoietic reconstruction. As such, the uses of OGP and its variants according to the present invention include the following:

1. Accelerate the engraftment of bone marrow transplants.
2. Enhance proliferation of transplanted stem cells and thus increase the availability of all types of hemopoietic cells including erythrocytes and platelets, thus relieve the need for supporting the host with these cells for at least several weeks.
3. Enhance the stromal hemopoietic microenvironment by increasing the stromal cell number and/or expression of stromal cell derived factors that support hemopoiesis.
4. Enhance the hemopoietic stem cell expression of receptors to factors that support hemopoiesis.
5. Enhance the "homing" of intravenous administered bone marrow transplants to the host bone marrow.
6. Enhance the restoration of blood cellularity after BMT.
7. Enable successful transplantation using reduced cell number, thus decreasing the number of (multiple) marrow extractions from donors, and enable the use of transplants as small as 10–15 ml (instead of 1000 ml).
8. Increase the number of hemopoietic totipotent and/or pluripotent stem cells in the donor peripheral blood, thus improving the feasibility of transplanting stem cells from peripheral blood.
9. Increase the number of hemopoietic stem cells in vitro in long-term bone marrow cultures for use as transplants; also a method to inhibit growth of tumor cells in allografts from leukemia patients.
10. Enhance the endogenous restoration of marrow and blood cellularity after chemo- and/or radiotherapy.
11. Enhance the restoration of population of resident macrophages after BMT or after chemo- and/or radiotherapy.

The polypeptides of the present invention can be included in pharmaceutical compositions for the treatment or prevention of diseases involving a reduction in bone formation as well as the other conditions discussed above.

The magnitude of a prophylactic or therapeutic dose of a polypeptide of this invention will, of course, vary with the group of patients (age, sex, etc.), the nature or the severity of the condition to be treated and with the particular polypeptide of this invention and its route of administration. In general, the daily dose range for bone formation enhancing use lies within the range of from about 4 pg to about 5 µg per kg body weight of a mammal.

Any suitable route of administration may be employed for providing a mammal, especially a human with an effective dosage of a polypeptide of this invention. For example, oral, rectal, topical, parenteral, ocular, nasal, sublingual, buccal, intravenous and the like may be employed. Dosage forms include tablets, troches, dispersions, suspensions, solutions, capsules, creams, ointments, aerosols and the like. Said dosage forms also include implanted slow releasing devices specifically designed for this purpose or other forms of implants modified to additionally act in this fashion.

The pharmaceutical compositions of the present invention comprise a polypeptide of this invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. The compositions include compositions suitable for oral, rectal, ophthalmic, pulmonary, nasal, sublingual, dermal, topical or parenteral (including subcutaneous, submucosol, intramuscular, intravenous and intra-arterial) administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the polypeptides of the present invention are conveniently delivered in the form of an aerosol spray presentation from pressurized packs or a nebuliser, or a powder which may be formulated as a cartridge from which the powder composition may be inhaled with the aid of a suitable device. The preferred delivery system for inhalation in a metered dose inhalation (MDI) aerosol, which may be formulated as a suspension or solution in fluorocarbon propellants.

Suitable topical formulations include transdermal devices, aerosols, creams, ointments, lotions, dusting powder, and the like.

In practical use, a polypeptide of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous and intra-arterial). In preparing the compositions for oral dosage form any of the usual pharmaceutical media may be employed, such as, for example, water glycols, oils, alcohols flavoring agents preservatives coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the polypeptides of this invention may also be administered by controlled release means and/or delivery devices.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

The following examples are offered by way of illustration and not by way of limitation.

EXAMPLE 1

(STAGE 1 PURIFICATION)
MATERIALS

Reagents for assay of alkaline phosphatase activity, collagenase type I, trypsin, soybean trypsin inhibitor-agarose (STI), BGJ medium (Fitton-Jackson modification), vitamin C, bovine pancreas insulin, and human serum albumin, were purchased from Sigma Chemical Co. (St. Louis, Mo). F-10 (Ham) medium (nutrient mixture), fetal calf serum (FCS), Dulbecco's PBS, and penicillin-streptomycin solution were obtained from Gibco (Chagrin Falls, Ohio). [methyl-$^3$H] Thymidine ([$^3$H]TdR) (5 mCi/mmol) was from Nuclear Research Center (Negev, Israel). Sephadex G-25 Sephadex G-75, and heparin-Sepharose CL-6B were purchased from Pharmacia (Uppsala, Sweden). Millipore membranes were from Schleicher & Schuell (Dassel, West Germany). Platelet-derived growth factor (PDGF) was purchased from Biomedical Technologies (Stroughton, Mass.) and human recombinant interleukin I-a(IL1) from cistrone (Pine Brook, N. J.). All other chemicals were of analytical grade and purchased from Merck AG (Darmstadt, West Germany). Tissue culture dishes were obtained from Nunc (Roskilde, Denmark). Rabbit polyclonal antiserum against PDGF was provided by Dr. C. E. Heldin (Uppsala University, Sweden).
METHODS
Preparation of Healing Marrow Conditioned Medium (HBMCM)

Tibial marrow was ablated from one limb of each of 400 g male rats of the Hebrew University (Sabra, Israel) strain as described previously. Bah, I. et al., (1985) Calcif Tissue Int 37:551. Briefly, a hole, 2 mm in diameter, was drilled in the shaft at a level below the proximal growth plate. Tissue was then removed from the marrow space with a polyethylene cannula inserted through the hole and attached to a high powered suction apparatus. The treated bones were dissected after 10 days and the shafts split longitudinally to expose the marrow space. Healing tissue was then removed from the endosteal aspect of the cortex, washed with copious amounts of serum-free F-10 medium supplemented with 1% (vol/vol) penicillin-streptomycin and incubated for 24 hour in the same medium (tissue from one limb/1 ml medium) at 37° C. in 5% $CO_2$-air. The medium was then collected and centrifuged for 30 min at 25,000× g, and the supernatant was filtered through a 0.45-mm pore-size Millipore membrane. The preparation was designated crude HBMCM; its protein content was 3–8 mg/ml. To remove cold thymidine, components of the tissue culture medium, and other low molecular weight contaminants, the crude EBMCM was subjected to gel filtration on a Sephadex G-25 column equilibrated with 5 mM ammonium-acetate. In standard experiments 6 or 35 mg protein were applied onto a PD-10 or 2.6×70 cm columns, respectively. Fractions were eluted with 5 mM ammonium-acetate and those containing protein in the void volume were pooled, lyophilized, and stored at −70° C. For further experiments samples were thawed and dissolved in PBS.

Monitoring Growth Promoting Activity to Osteoblastic Cells

Growth factor activity (GFA) was monitored by examining effects on DNA synthesis in a culture of osteoblastic rat osteosarcoma cells (ROS 17/2). Stock cultures of ROS-17/2 cells were maintained in F-10 medium containing 10% FCS. To study the mitogenic effect of different preparations, confluent cultures were trypsinized, and $2\times10^4$ cells seeded in 2 $cm^2$ culture wells (16 mm multiwell dishes) in F-10 medium and incubated at 37° C. in $CO_2$-air. During the first 6 h the medium was supplemented with 2% FCS to enhance cell anchorage. This was followed by 18 hour incubation in serum-free medium that contained the test preparation added as protein solution in PBS. To determine DNA synthesis rates, cultures were pulsed with [$^3$H]TdR, 1.5 mCi/well, for the last 2 hour of the incubation period. The pulse was terminated by washing twice with ice cold 10% (wt/vol) trichloroacetic acid and with ethanol-ether (3:1, vol/vol). After the cell layer had dried, the trichloroacetic acid-insoluble material was dissolved in 0.2M NaOH and its total radioactivity estimated by liquid scintillation spectrometry. Data were expressed as growth factor units (GFU). Since the growth of ROS cells is serum dependent, 1 U was defined as half the effect of 10% FCS in a given experiment. Cell number was determined in sister cultures exposed to test preparations for 48 hour. This was done after trypsinization using a fixed volume hemocytometer. The data were expressed as the number of cells per culture well.

Partial Purification of GFA from HBMCM Effect of Heat

One milliliter aliquots of HBMCM containing 0.5–1.0 mg protein were left at room temperature or heated to 56° C. for 30 or 60 min. Similar samples were also tested for stability of the GFA to boiling for 10 min. Since the GFA was found to be stable to the boiling procedure (Table 1) a boiling step was used for the removal of extraneous protein by denaturation and centrifugation for 45 min at 25,000× g.

Affinity Chromatography

A heparin-Sepharose column (0.9×25 cm bed volume) was prepared according to manufacturer's instructions, packed with PBS, and pumped at room temperature at a flow rate of 0.6 ml/min. Preliminary experiments using heparin-Sepharose batchwise indicated that at equilibrium with 0.15M NaCl (PBS) the GFA was left unbound to the insoluble substrate. Thus, a 2-ml sample containing 30 mg boiled HBMCM in PBS was loaded onto the column and eluted by washing the bed with 24 ml PBS. The eluate was dialyzed for 24 h against 5 mM ammonium acetate, assessed for protein, and lyophilized.

Gel Filtration

To further purify the HBMCM-derived factor(s), 0.5–6.0 mg/ml of protein that was recovered from the heparin-Sepharose column were dissolved in 1 ml of 5 mM ammonium acetate and applied onto a 1.2×54 cm Sephadex G-75 column equilibrated with the same solution. The protein samples were eluted at room temperature using 5 mM ammonium acetate at a flow rate of 0.65 ml/min. Fractions of 1.3 ml were assessed for protein and lyophilized.

Tryptic Digestion

To confirm the proteinaceous nature of the HBMCM-derived factor, 1-ml aliquots of HBMCM after the heparin-Sepharose step were incubated with trypsin (trypsin/HBMCM ratio 1:20 wt/wt) at 25° C. The reaction was stopped after 30 min by applying the mixture to a column of STI (0.4×1 cm). Controls consisted of samples treated similarly but without trypsin in the reaction mixture.

Other Cell and Organ Cultures

To study the specificity of the HBMCM-derived factor to osteogenic cells, active preparations were further tested for their mitogenic effect on osteoblastic and nonosteoblastic fetal rat calvarial cells (FRC cells), and nonosteogenic rat osteosarcoma cells (ROS 25/1). Cultures were uniformly kept at 37° C. in $CO_2$-air. In all experiments test preparations were added to cultures as protein solutions in PBS.

ROS Cells

ROS 25/1 cells were cultured and tested using a protocol similar to that reported above for ROS 17/2 cells.

FRC cells

Cells obtained from parietal bones of 21-day rat fetuses were used in primary cultures. Five cell populations were separated by sequential digestion with collagenase and trypsin according to the method described by Luben et al., (1976) Endocrinology 99:526. Calls from populations 1–2 and 3–5 were pooled and designated nonosteoblastic and osteoblastic, respectively. The cells were seeded in 16-mm multiwell dishes, $3\times10^4$ cells per well, and allowed to grow for 24 h in F-10 medium supplemented with 10% FCS. The medium was then replaced by one with 1% FCS, and after 24 h the test preparation and [$^3$H]TdR, 1.5 mCi/well, were added incorporation of [$^3$H]TdR into DNA and cell number were assessed as described above after an additional 24-hour period.

Fetal Mouse Long Bone

This was carried out as described by Soskolne et al., (1986) bone 7:41. Briefly, radii and ulnae were removed from 16-day fetuses and dissected free of muscle and soft tissue. They were then cultured in a chemically defined medium (BGJ, Fitton-Jackson modification) supplemented with 150 mg/ml vitamin C and 4 mg/ml human serum albumin. Phosphate concentration was adjusted to 1 mM. Total and diaphyseal lengths of individual bone rudiments were measured at the beginning of the culture period and after 48 hour directly under a dissecting microscope using transmitted light. Elongation, either total or diaphyseal, was calculated as the difference between these measurements, and the results were expressed as the ratio between bones treated with growth factors and controls grown in a chemically defined medium only (T/C ratio).

Alkaline Phosphatase Activity

For this assay the medium was removed from cultures of ROS 17/2 cells, and the cells were washed with PBS, scraped into distilled water, and sonicated. Enzyme activity was assayed with p-nitrophenyl phosphate as a substrate as described by Ashton et al., (1984) Calcif Tissue Int 36:83. The results were expressed as micromoles of p-nitrophenol released per min/$10^6$ cells that were counted in sister cultures.

Protein Content

Protein was determined according to the method of Bradford, (1976) Anal. Biochem. 72:248.

Assessment of IL1 Activity

IL1 activity was estimated using a thymocyte proliferation assay as described by Barak et al., (1986) J. Biol. Response Modifies 5:362.

Assay for PDGF

Anti-PDGF antibody neutralization experiments were carried out with polyclonal antiserum prepared in rabbits against PDGF. PDGF or HBMCM-derived preparations were added to ROS 17/2 cells in the presence or absence of antibody and examined for effects on [$^3$H]TdR incorporation.

RESULTS

The effect of crude HBMCM on the number and alkaline phosphatase activity of ROS 17/2 cells is established. At the highest dilution of crude HBMCM (1:200) there was a 75% decrease in cell number and more than 2-fold increase in enzyme activity. At lower dilutions, 1:100–1:10, the number of cells was approximately 2-fold higher compared to untreated cultures, and alkaline phosphatase activity showed a dose-dependent reduction.

When crude HBMCM was subjected to gel filtration on Sephadex G-25 column, approximately 80% of the added protein was recovered in fractions comprising the void volume. These fractions contained nearly all of the (94%) mitogenic activity eluted from the column.

Partial Purification of GFA From HBMCM Effect of heat on GFA.

The effect of heat on HBMCM-derived GFA is summarized in Table 1. GFU are growth factor units. 1 U is defined as half the effect of 10% FCS in the same experiment.

TABLE 1

Effect of heat on HBMCM mitogenic activity ([$^3$H]TdR incorporation into DNA) in serum-free ROS 17/2 cell culture

| Factor[a] | Counts per min[b] | GFU[b] |
|---|---|---|
| HBMCM (60 min, RT) | 2038 ± 304 | 0.29 ± 0.05 |
| HBMCM (30 min, 56 C.) | 2792 ± 125 | 0.59 ± 0.07 |
| HBMCM (60 min, 60 C.) | 3213 ± 89 | 0.82 ± 0.05 |
| HBMCM (10 min, boiling) | 5820 ± 243 | 2.82 ± 0.18 |
| Serum-free control | 1676 ± 130 | |
| Serum (10%) control | 5385 ± 350 | |

RT, Room temperature.
[a]Factor concentration was 3.6 mg/ml.
[b]Mean ± SE of four replicate culture wells.

With the elevation of either temperature or exposure time, there was an increase in the stimulatory effect of HBMCM on [$^3$H]TdR incorporation into DNA of ROS 17.2 cells. In particular, there was a marked increase in mitogenic activity after 10 min boiling; the mitogenic effect of the supernatant obtained by boiling and centrifugation was similar to that of FCS. Half the protein could be removed by boiling and centrifugation with 8-fold increase in specific activity (Table 2). The dose-response relationship of the boiled preparation in the ROS 17/2 cell assay indicated significant GFA at 0.5–5 mg/well with a decline at higher doses. Activity of the boiled preparation was also noted when 0.5 mg was added to cultures of a pool of FRC cell populations 3–5 (osteoblastic population).

TABLE 2

Partial purification of HBMCM-derived growth factor by boiling and affinity chromatography on heparin-Sepharose

| Step of Purification | Protein (mg)[a] | Recovered Activity (GFU) | Specific Activity (GFU/mg) | Purification |
|---|---|---|---|---|
| Sephadex G-25 | 5 | 495 | 99 | 1 |
| Boiling | 2.5 | 2,230 | 822 | 8 |
| Heparin-sepharose | 0.5 | 30,000 | 60,000 | 606 |

[a]From 1 ml crude HBMCM.

Affinity Chromatography.

When boiled HBMCM was loaded onto a heparin-Sepharose column, 20% of the applied protein was eluted by PBS, with the remaining protein left bound. The mitogenic activity recovered in the fraction eluted by PBS represented a 13 fold increase in specific activity (Table 2). The enhancement of GFA after the heparin-Sepharose step is also shown by the dose-response relationship where the effect on ROS 17/2 cells was apparent at 50 ng/well. The peak stimulation of DNA synthesis rate was found at 0.5 µg/well with a decline thereafter. The preparation obtained using heparin-Sepharose had also a considerable mitogenic effect on osteoblastic FRC cells. When material recovered from the heparin-Sepharose column was subjected to tryptic digestion, there was more than 95% inhibition of HBMCM derived GFA (Table 3).

TABLE 3

Effect of tryptic digestion on stimulation of ROS 17/2 cell DNA synthesis by HBMCM chromatographed on heparin-Sepharose

| Preparation added[a] | Counts per min[b] | GFU[b] |
|---|---|---|
| HBMCM[c] | 7245 ± 357 | 3.59 ± 0.28 |
| HBMCM + STI[d] | 6309 ± 683 | 2.89 ± 0.52 |
| HBMCM + trypsin + STI | 1502 ± 69 | 0.13 ± 0.05 |
| Serum-free control | 1330 ± 75 | |
| Serum (10%) control | 3998 + 68 | |

[a]In absence of serum unless otherwise specified.
[b]Mean ± SE of four replicate culture wells.
[c]Two micrograins per culture of HBMCM preparation obtained by heparin-Sepharose chromatography.
[d]Two micrograms per culture of HBMCM preparation obtained after heparin-Sepharose and soybean trypsin inhibitor (STI)-agarose chromatograph.

Gel Filtration on Sephadex G75

The elution profile of GFA from the Sephadex G75 column visualized by enhancement of [$^3$H]TdR incorporation into DNA of ROS 17/2 cells was established. Most of the protein and some mitogenic activity eluted close to the void volume of the column. Three major peaks of activity eluted in fractions 19 to 38. Based on the elution positions of mol wt markers, the mol wt estimates of the three peaks were 35,000, 19,000 and less than 10,000.

Effect of HBMCM-derived Preparations In Other Cell and Organ Cultures

Nonosteoblastic ROS 25/1 cells had been obtained from the same tumor as ROS 17/2 cells but unlike the latter they do not express the osteoblastic phenotype. HBMCM-derived preparations, in particular those obtained after the heparin-Sepharose step, elicited some mitogenic response in the ROS 25/1 cell culture at concentrations similar to those stimulatory to ROS 17/2 cells. However, the magnitude of the ROS 25/1 cell response, was considerably smaller compared to that of ROS 17/2 cells. In addition, the HBMCM-derived preparations did not have an apparent effect on DNA synthesis rates of nonosteoblastic FRC cells (populations 1–2).

When boiled HBMCM was added to an organ culture of fetal radii and ulnae there was a marked dose-dependent enhancement of growth expressed by increases in both diaphyseal and total elongation.

The peak effect was found at 8 µg/ml protein concentration. At this concentration the increase of diaphyseal and total lengths was approximately 200% and 250% over growth factor-free controls, respectively. The difference in the magnitude of elongation between the diaphysis and whole rudiment resulted from enhanced growth of the cartilaginous epiphyseal ends. The peak effect of boiled HBMCM was nearly twice that of a positive insulin control.

Thymocyte Proliferation Assay for IL1 Activity

Table 4 shows that unlike IL1 preparations, in medium containing PEA, neither boiled HBMCM nor the derivative obtained after the heparin-Sepharose step stimulated [$^3$H]TdR incorporation into thymocyte DNA, suggesting that the HBMCM-derived growth factor does not resemble IL1.

TABLE 4

Effect of IL1 and HBMCM preparations on incorporation [$^3$H]TdR into DNA of isolated murine thymocytes

| Factor[a] | Concentration | Counts per min[b] |
| --- | --- | --- |
| Boiled HBMCM | 0.4 µg/ml | 1770 ± 13 |
|  | 4.0 µg/ml | 1613 ± 11 |
| HS-HBMCM[c] | 0.7 µg/ml | 2667 ± 5 |
|  | 1.1 µg/ml | 2290 ± 17 |
| IL1[d] | 5.0 U/ml | 7634 ± 35 |
| IL1[e] | 5.0 U/ml | 6532 ± 30 |
| PHA | 10.0 µg/ml | 2590 ± 20 |
| –PHA |  | 400 ± 46 |

[a]HBMCM and IL1 preparations were tested in the presence of 10.0 mg/ml PHA.
[b]Mean ± SE of eight culture microwells.
[c]HBMCM after heparin-Sepharose step.
[d]From human monocytes.
[e]Human recombinant.

PDGF Content

Addition of polyclonal anti-PDGF antibodies to ROS 17/2 cells inhibited PDGF-stimulated replication but did not reduce the mitogenic effect produced by intermediate doses of boiled HBMCM and the preparation obtained after the heparin-Sepharose step. Under these conditions the presence of a significant amount of PDGF in the HBMCM-derived preparations should have resulted in decreased enhancement of ROS cell proliferation when tested with the antiserum.

EXAMPLE 2

(STAGE 2A PURIFICATION)
MATERIALS AND METHODS
Materials

F-10 (HAM) medium (nutrient mixture), fetal calf serum (FCS), Dulbecco's phosphate buffered saline (PBS) and penicillin-streptomycin solution were obtained from Gibco (Chagrin-Falls, Ohio). [methyl-$_3$H]thymidine ([$^3$H]TdR) (5 µCi/mmol) was from Nuclear Research Center (Negev, Israel). Heparin-Sepharose CL-6B was purchased from Pharmacia (Uppsala, Sweden). Reagents for alkaline phosphatase assay were obtained from Sigma (St. Louis, Mo.) and chemicals for SDS-PAGE from Bio-Rad (Richmond, Calif.). Transforming growth factors beta 1 (TGFβ1) and beta 2 (TGFβ2) were obtained from R&D Systems (Minneapolis, Minn.). Insulin-like growth factor I (IGF-I) was obtained from Merck, Sharp and Dohme Research Laboratories, Rahway, N.J. All other chemicals were of analytical grade and purchased from Merck AG (Darmstadt, W. Germany). Rat osteosarcoma (ROS) cells were obtained from Drs. G. A. and S. B. Rodan (Merck, Sharp and Dohme Research Laboratories, West Point, Pa). Tissue culture dishes were obtained from Nunc (Roskilde, Denmark).

Preparation of Healing Marrow Conditioned Medium (HBMCM)

Conditioned medium was prepared from healing marrow as described previously by Bah, I. et al (1988) Endocrinology 123:345. Briefly, tissue was separated from the marrow space of rat tibiae 10 days after ablation and incubated for 24 hours in serum-free F-10 medium supplemented with 1% (vol./vol.) penicillin-streptomycin at 37° C. in 5% $CO_2$-air. The medium was then collected, boiled for 10 minutes, centrifuged for 30 minutes at 25,000× g and filtered through 0.45-µm pore size Millipore membrane.

Cell Cultures.

Growth factor activity (GFA) was monitored by examining effects on DNA synthesis in a culture of osteogenic ROS 17/2 cells. In short, HBMCM-derived preparations and other growth factors were added to 2 cm$^2$ culture wells (16 mm multiwell dishes) containing the ROS cells in serum-free F-10 medium. After 22 hours, the cultures were pulsed with $^3$H]TdR, 2 µCi/ml. Two hours later, the total radioactivity of trichloroacetic acid insoluble material was determined by liquid scintillation spectrometry and the data expressed as percent over untreated cultures or growth factor units (GFU). One unit was defined as half the effect of 10% fetal bovine serum in a given experiment. To assess specificity of the HBMCM derivatives to osteogenic cells, some preparations were tested in cultures of non-osteogenic ROS 25/1 cells using a protocol similar to that described above for the ROS 17/2 cells.

Affinity Chromatography

A heparin-Sepharose column (0.9×25 cm bed volume) was prepared according to the manufacturer's instructions, packed with PBS and pumped at room temperature at a flow rate of 0.5 ml /minutes. A 2 ml sample containing 28 mg boiled HBMCM in PBS was loaded onto the column and eluted in two steps. First, the heparin-Sepharose bed was washed isocratically with PBS for 200 minutes. Then a two-stage linear gradient of 0.15–1.35M NaCl in phosphate buffer, pH 7.2, was pumped through the column The gradient rate was 0.015 M/minute and 0.005 M/minute during stages I and II, respectively. Two ml fractions were collected and dialyzed for 24 hours against 5 mM ammonium-acetate, assessed for protein and lyophilized.

Inactivation Experiments

Samples of heparin-Sepharose peak activity fractions containing approximately 10 GFU were dissolved in water and reacted for 90 minutes at 37° C. with (a) 5 mM dithiothreitol (DTT); (b) 0.1M HCl and (c) PBS control. The reactions were terminated by 5 hours dialysis against 5 mM ammonium acetate in the cold.

Gel Electrophoresis

SDS-PAGE was performed in 1.5 mm thick 10–18% gradient gels according to Laemmli, Nature 227,680 (1970).

Alkaline Phosphatase Activity

For this assay ROS 17/2 cells were grown for 48 hours in F-10 medium supplemented with 2% FBS. During the last 24 hours, the cells were challenged with 10 µg/ml of either boiled or unboiled conditioned medium or 2 µg/ml of the heparin-Sepharose peak activity fractions. Then the medium was removed from the cultures and the cells washed with PBS, scraped into distilled water, and sonicated. Enzyme activity was assayed with p-nitrophenol phosphate as substrate. The results were expressed as micromoles of p-nitrophenyl released per min/$10^6$ cells that were counted in sister cultures.

Protein Content

Protein was determined according to the method of Bradford, Anal. Biochem. 72,248 (1976).

RESULTS

The elution profile of GFA from the heparin-Sepharose column, visualized by enhancement of [$^3$H]TdR incorporation into DNA of ROS 17/2 cells was obtained.

TABLE 5

Heparin-Sepharose chromatography of HBMCM-derived growth factor activity: elution time[1] and maximal peak activity[2]

| Peak | Elution time (min) | Maximal activity (GFU) | Total protein (mg) |
|---|---|---|---|
| Stage I: isocratic elution with 0.15M NaCl | | | |
| AII | 56.4 | 0.62 ± 0.06 | 3.12 |
| AI | 130 | 1.35 ± 0.05 | 0.61 |
| AIII | 184 | 1.02 ± 0.04 | 0.13 |
| Stage II: elution with 0.15–1.35 NaCl gradient | | | |
| BI | 7.3 | 1.00 ± 0.04 | 1.06 |
| BII | 39 | 1.59 ± 0.02 | 0.80 |
| BIII | 130 | 0.84 ± 0.04 | 0.06 |

[1]Elution time is presented separately from the onset of each stage.
[2]Fraction samples assayed for activity contained 2 mg/ml protein. Data are mean ± SE of three replicate cultures per condition.

Three major peaks of activity, AI, AII and AIII, eluted when the column was washed isocratically with PBS (Table 5). Preparation A-I and particularly A-II were fairly stable to reduction with DTT and acidification with HCl (Table 6).

TABLE 6

Stability of HBMCM-derived GFA peaks separated by heparin-Sepharose chromatagraphy

| Treatment | A-I | A-II | B-II |
|---|---|---|---|
| | % activity remaining | | |
| Boiling (HBMCM) | 100 | 100 | 100 |
| 5 mM DTT | 68 | 91 | 5 |
| 0.1M HCl | 68 | 77 | 75 |

The resistance to reduction was further confirmed by gel electrophoresis where both A-I and A-II appeared similar on reduced and non-reduced gels. A-II contained a component migrating close to the gel's front and a few additional species of 60–75 KD. A-I consisted of several components at the 55–90 KD range. When the column was pumped with an NaCl concentration gradient. The respective GFA peaks, designated B-I, B-II and B-III, resolved at 0.3, 0.75 and 1.2M salt, respectively. Preparation B-II was inactivated by reduction (Table 6) and on reduced gel s showed several 55-80 KD bands in addition, B-I and B-II contained 14 and 33 KD bands, respectively. The amount of protein recovered in preparations A-III and B-III was insufficient for their testing in the inactivation and electrophoresis experiments.

The conditioned medium prior to boiling failed to influence ROS cell alkaline phosphatase. Preparations A-II, B-II and B-III stimulated enzyme activity almost two-fold. The highest stimulatory effect, however, was seen when HBMCM was tested (300%).

Nonosteogenic ROS 25/1 cells had been obtained from the same tumor as ROS 17/2 cells but unlike the latter they do not express the osteogenic phenotype. Preparation A-II failed to stimulate incorporation of [$^3$H]TdR into DNA of the ROS 25/1 cells. A-I showed some stimulation which was, however, only 40% its effect on ROS 17/2 cells. B-I had a similar effect on both cell types.

DISCUSSION

During the osteogenic phase regenerating bone marrow produces growth-promoting activity to osteogenic cells. The present results show that the activity in HBMCM is divided among at least six independent activities separable by heparin-Sepharose affinity chromatography. Similarly, it has been demonstrated that growth factor activity obtained tom demineralized bone matrix consists of several proteinous species also separable on heparin-Sepharose. Although multiple peaks in HBMCM could theoretically result from proteolytic degradation or aggregation of a factor with different "carrier" protein, this is unlikely since (a) inclusion of proteinase inhibitors during the medium conditioning and further processing did not alter the elution profile from heparin-Sepharose (data not shown) and (b) the properties of the separate GFA peaks with regard to stability and target cell action are clearly distinct.

EXAMPLE 3

(STAGE 2B: PURIFICATION AND AMINO ACID SEQUENCING OF OGP)

MATERIALS

F-10 (HAM) medium (nutrient mixture) and kanamycin sulfate were obtained from Grand island Bological (Grand Island, N.Y). Fetal bovine serum (FBS) was from Hazelton/KC Biologicals (Leneta, Kans.). [methyl-$^3$H]Thymidine ([$^3$H]tdR) (6.7 Ci/mmol) was purchased from New England Nuclear (Boston, Mass.) Trans-epoxysuccinyl-leucyl-amido(4-guanidino)butane (E64), leupeptin and pepstatin were from Sigma Chemical Co. (St. Louis, Mo). Heparin-Sepharose CL-6B and Sephadex G25 were obtained form Pharmacia (Uppsala, Sweden). Tissue culture dishes were the product of Costar (Cambridge, Mass.).

METHODS

Partial purification of GFA from HBMCM:

HBMCM was prepared as described above (Example 1 and 2) and partially purified by boiling and Heparin-Sepharose chromatography using a modification of the protocol reported in Bah I., et. al (1988) Edocrinology 123:345. The HBMCM was boiled for 10 min and then centrifuged at 25,000× g for 45 minutes in a cooled centrifuge. The supernatant was collected and supplemented with the following proteinase inhibitors: 25 μM E64, 25 μM leupeptin and 5 μM pepstatin. The same minute of proteinase inhibitors was also added to preparations recovered from the subsequent heparin-Sepharose, gel filtration and ion-exchange steps (see below).

Affinity Chromatography

A heparin-Sepharose column (1.6×24 cm bed volume) was prepared according to manufacturer's instructions, equilibrated with phosphate buffered saline (PBS) which was pumped at a flow rate of 0.5 ml/min at 4° C. Boiled HBMCM containing 100 mg protein was passed through the column. The column was further washed with 50 ml PBS. The recovered conditioned medium and PBS were then pooled and lyophilized. The heparin-Sepharose step was carried out repeatedly to accumulate partially processed GFA in amounts sufficient for further purification.

Monitoring GFA in Osteogenic Cells

This was carried out in osteoblastic ROS 17.2 cells as described above (Example 1) with the exception that kanamycin-sulfate replaced the penicillin-streptomycin. The results were expressed as GFU or percent over PBS controls.

Ion Exchange Chromatography

To remove salts, cold thymidine and other components of the tissue culture medium, the preparation recovered from the heparin-Sepharose column was dissolved in a small volume of water and passed over a prepacked Sephadex G25 column (PD-10). Ammonium-acetate (5 mM) was used for column equilibration and elution. The void volume from multiple columns was collected and fractions showing GFA in the ROS 17.2 cell assay were pooled and lyophilized.

For ion-exchange chromatography 50 mM sodium acetate buffer (SAB), pH=5.0 was added to the lyophilized material, 1 ml/1.65 mg protein. The mixture was centrifuged at 10,000× g for 15 min and the pellet, which contained about 85% of the protein in the mixture, was discarded. Samples of the supernatant containing 0.4–7.0 mg protein were chromatographed on a Mono-S HR 5/5 fast protein liquid chromatography (FPLC) cation exchange column (Pharmacia Uppsala, Sweden ) using Waters 650 Advanced Protein Purification System (Millipore Corporation, Milford, Mass. The column was pumped at a flow rate of 1 ml/min in three stages: i. 3 min isocratically with the initial SAB; ii. 30 min linear gradient with 0–1.0M NaCl in SAB and iii. 7 min with 1.0M NaCl in SAB. One ml fractions were collected and samples containing approximately 30 ng protein were assayed for GFA. The results for each fraction were expressed as the percent of paired control samples consisting of the corresponding fractions obtained from the column during an identical run without loading the protein.

Reverse-phase Chromatography

Fractions from multiple ion-exchange runs showing GFA were pooled and 3.2 ml with an estimated total protein content of 18 µg were loaded onto C1/C8 ProRPC HR 5/2 FPLC reverse-phase column (Pharmacia, Uppsala, Sweden). The column was eluted with 0–100% acetonitrile gradient containing a 0.1% trifluoroacetate (TFA) at a flow rate of 0.5 ml/min. The fractions, 0.5 ml each, were collected and dried in a Speedvac concentrator (Savant, Farmingdale, N.Y.) Prior to this, 10 µl aliquots from each fraction were dried separately, redissolved in PBS and assayed for GFA.

Amino acid sequencing:

Fractions recovered from the reverse-phase column that showed GFA were pooled and a sample containing ~30 ng protein was subjected to automated Edman degradation for amino acid sequencing in a gas-phase protein sequencer Model 470A equipped with an on-line PTH analyser, Model 120A (Applied Biosystems, Inc., Foster City, Calif.

Protein Content

Protein was determined as described above (Example 1).

RESULTS

Reverse-phase chromatography

Figure 1:
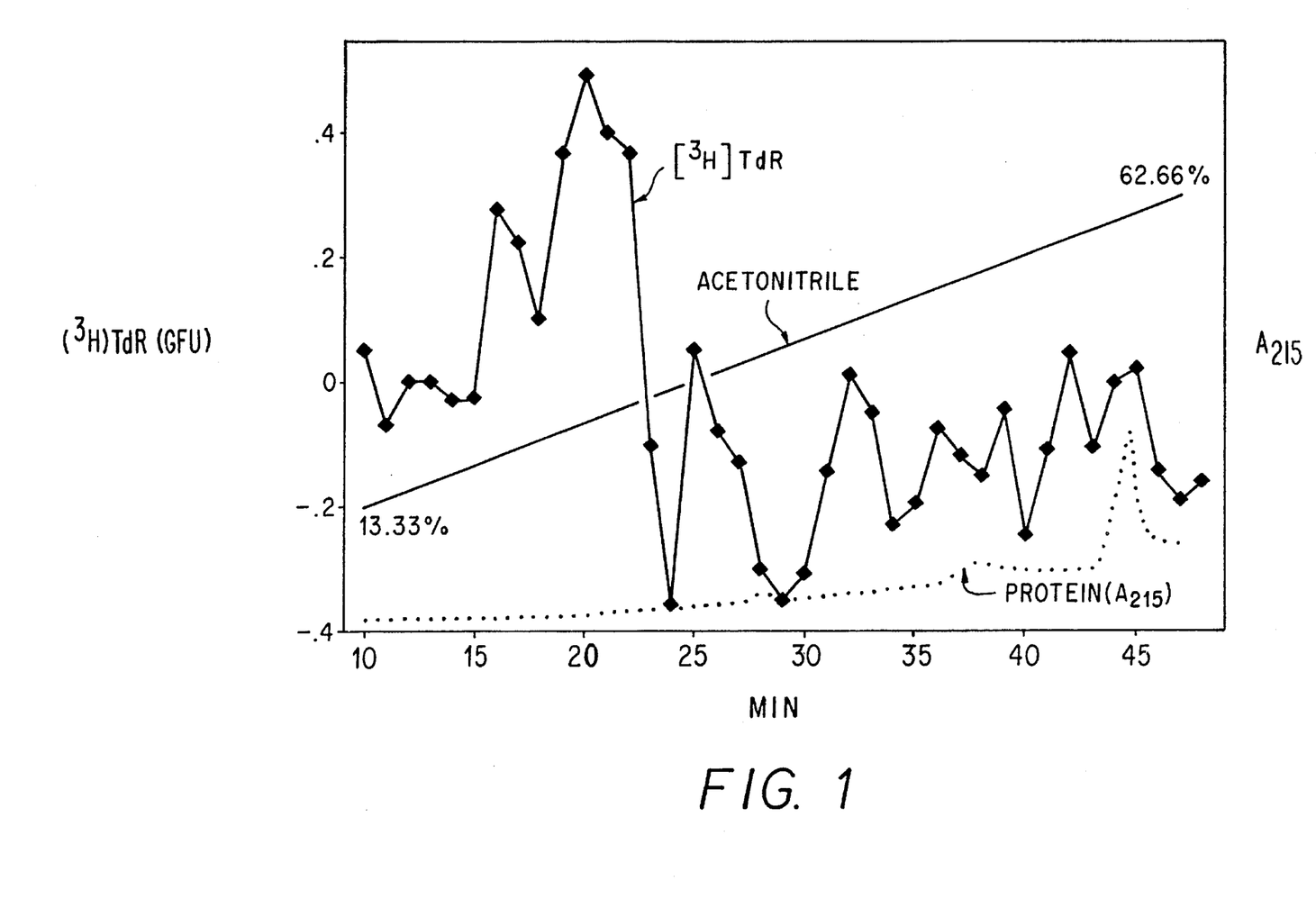
FIG. 1 shows C1/C8 reverse-phase chromatography of GFA obtained by cation-exchange chromatography. The solid line represents DNA synthesis rates in ROS 17/2 cell cultures. Data are mean counts per minute from triplicate cultures. All fractions in the peak region as well as all other data points had an SD<10% of the mean. Dotted line represents the protein content.

The elution profile of reverse-phase chromatography is shown in FIG. 1. Protein was recovered in two minor peaks (elution time 27 and 36 min) and one major peak (elution time 45 min). A major GFA peak was recovered after 19–22 min, an elution time corresponding to ~27% acetonitrile.

The amino acid sequence of the protein recovered in the mitogenically active fractions (elution time 19–22 min, FIG. 2) revealed a 14-residue peptide, MW 1523. There was no evidence for the presence of other contaminating peptides in this preparation. The sequence is shown in Table A.

EXAMPLE 4

(BIOLOGICAL ACTIVITY OF SYNTHETIC OGP)

MATERIALS t-Boc-Gly OCH$_2$-Pam resin, N-Boc protected amino acid derivatives, N,N dicyclohexylcarbodiimde (DDC), 1-hydroxybenzotriazole (HOBT), diispropylethylamine (DIEA), trifluoroacetic acid (TFA), N,N dimethylformamide (DMF) and dichloromethane (DCM) were obtained from Applied Biosystems Inc. (Foster City, Calif.). Hydrogen fluoride (HF) was purchased from Matheson (Secacus, N.J.), p-Cresol from Aldrich Chemical Co. (Milwaukee, Wis.) and Sephdex G15F from Pharmacia (Uppsala, Sweden). F-10 (HAM) medium (nutrient mixture) and kanamycin sulfate were obtained form Grand Island Biological (Grand Island, N.Y.) and fetal bovine serum (FBS) was from Polysciences Inc. (Warrington, Pa.). Male Sprague-Dawley rats weighing 240–260 g were from Taconic Farm, N.Y. Achromycin (tetracycline hydrochloride) was from Lederle (Pearl River, N.Y.) and Terramycin (oxytetracycline) from Roerig-Pfizer (New York, N.Y.). Ingredients of methyl-methacrylate embedding resin were the product of Fischer Scientific (Fair Lawn, N.J.).

METHODS

Preparation of synthetic OGP (sOGP)

sOGP was synthesized by the solid phase method of Merrifield (1969) Adv. Enzymol. 32:221 using an Applied Biosystems Model 430A Automated Peptide Synthesizer.(Applied Biosystems Inc., Foster City, Calif.). The synthesis was carried out on 0.5 mmol t-Boc-Gly-OCH$_2$-Pam resin (1% crosslinked, 0.78 mmol/g). The amino acid derivatives were protected on the α-amino function by t-butyloxycarbonyl (Boc) groups. Protection of the side chains was as follows: Arg (Tos), Lys (2-Cl—Z), Tyr (2-Br—Z) and Thr(O-Bzl ). Coupling of the Boc protected derivative of Arg and Gln was by the DCC-HOBT method of Konig, W. and Geiger, R. (1970) Chem. Ber., 103:788. All other amino acid derivatives were coupled via the DCC-mediated preformed symmetrical and anhydride method of Hagemaier, E. and Frank H. (1972) Hoppe-Seyler's Z. Physiol. Chem. 353:1973. The coupling of each amino acid residue was repeated twice. Deprotection of the blocked amino-terminus was by treatment with 60% TFA in DCM. Side chains were deprotected and the peptide was cleaved from the resin (2.7 g resin-bound peptide) using the HF procedure where a minute of 4 ml anisole and 36 ml liquid HF was used for 75 min at 0° C. The crude synthetic peptide was partially purified on a Sephadex G15F 3×35 cm column eluted with 50% (v/v) aqueous acetic acid. Further purification was accomplished on a Waters DeltaPrep 3000 High Pressure Liquid Chromatography instrument equipped with a PrePak 1000 module (Millipore Corporation, Milford, Mass.) The cartridge was pumped with 5–33.5% acetonitrile gradient containing 0.1% TFA at a flow rate of 100 ml/min.

The effect of sOGP on bone in vivo sOGP in PBS solution was administered to rats daily via the tail vein, 100 µl/day/rat for 8 days. Control animals received PBS alone or a peptide having the reverse sequence sOGP, The rats were labeled twice with tetracycline by intramuscular injections of 6 mg achromycin and terramycin (in water) on days 2 and 8, respectively. The animals were sacrificed by-cervical dislocation and the tibiae where separated and fixed in 70% ethanol. The specimens were then dehydrated, embedded in methyl-methacrylate and 10 mm undecalcified, unstained sections were subjected to fluorescent microscopy. Fluorescent images were recorded using a 480 nm fluorescin filter in a Microphot epifluorescent microscope (Nikon, Japan) equipped with a SIT video camera (Dage-MTI, Michigan City, Ind.) connected to a Magiscan interactive image analyzer (Joyce-Loebl, Gateshead, UK). Measurements in the cortico-endosteal surface and the surface of the proximal metaphyseal trabeculae, were carried out on the analyzer screen at ×550 magnification. Separation of double labels was determined as the mean of multiple measurements between the center of the lines in all double labeled zones in 10 microscopic fields. Mineral apposition rate (MAR) was expressed as micrometers per day of interlabel time space.

RESULTS

Figure 2A:
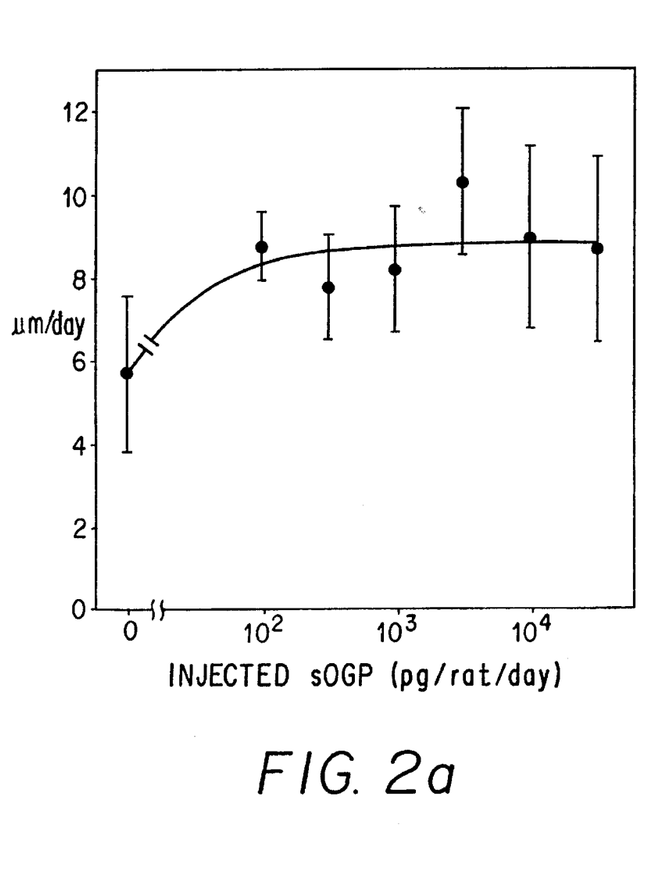
FIG. 2 shows the effect of sOGP on mineral appositional rate (MAR) in cortico-endosteal (a) and metaphyseal trabecular (b) surfaces of rat tibia. Data are mean±SD of measurements in 4 (100 and 300 pg groups) or 5 (other groups) rats, one tibia per animal.
Figure 2B:
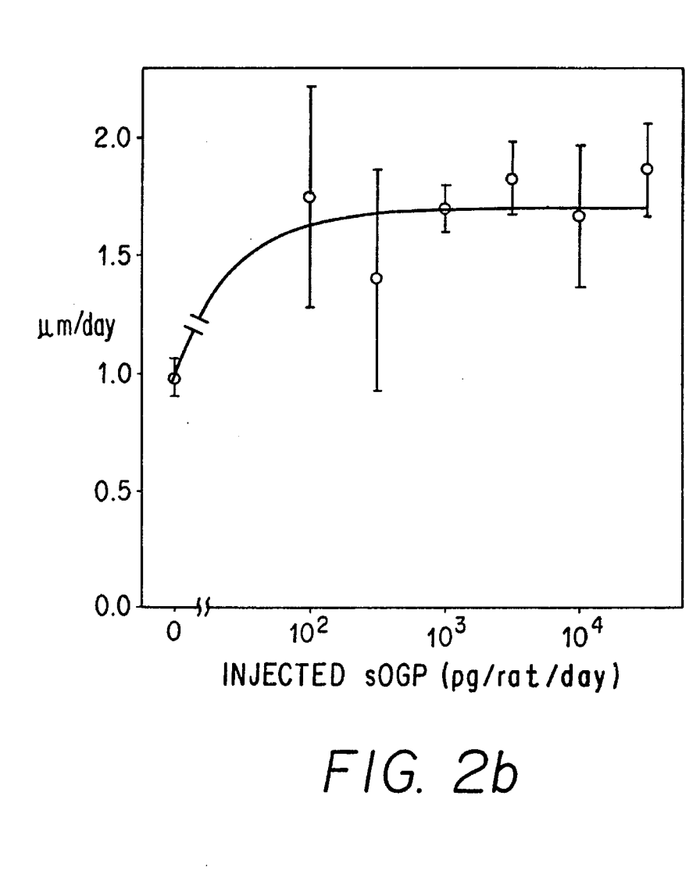

Following 8 intravenous injections of sOGP both cortico-endosteal and metaphyseal trabecular surfaces of the tibia showed increase MAR (FIG. 2). The effective dose range was 0.1–30 ng/rat/day.

EXAMPLE 5

(EFFECT OF sOGP ON ENGRAFTMENT OF BONE MARROW TRANSPLANT)

METHODS sOGP in phosphate buffered saline was administered to female C57 Black mice, weight 25 grams, by subcutaneous injections of 100 μl given once daily, for 12 days. The daily dose ranged from 0.0005 to 5 nmol per mouse. The control animals received phosphate buffered saline only. On day 8 after the onset of sOGP treatment the mice received total body X-ray irradiation consisting of a single 900 rad dose using a $^{60}$Co source (Picker C-9, 102.5 rad/min). This was followed immediately by an intravenous injection of $10^5$ unselected syngeneic bone marrow cells. The animals were killed 14 days after the onset of sOGP treatment, both femurs were dissected out and their epiphyseal ends removed. The bone marrow was washed out completely into phosphate buffered saline. A single cell suspension was prepared by drawing the preparation several times through graded syringe needles and the cells were counted in a hemocytometer.

RESULTS

Figure 3A:
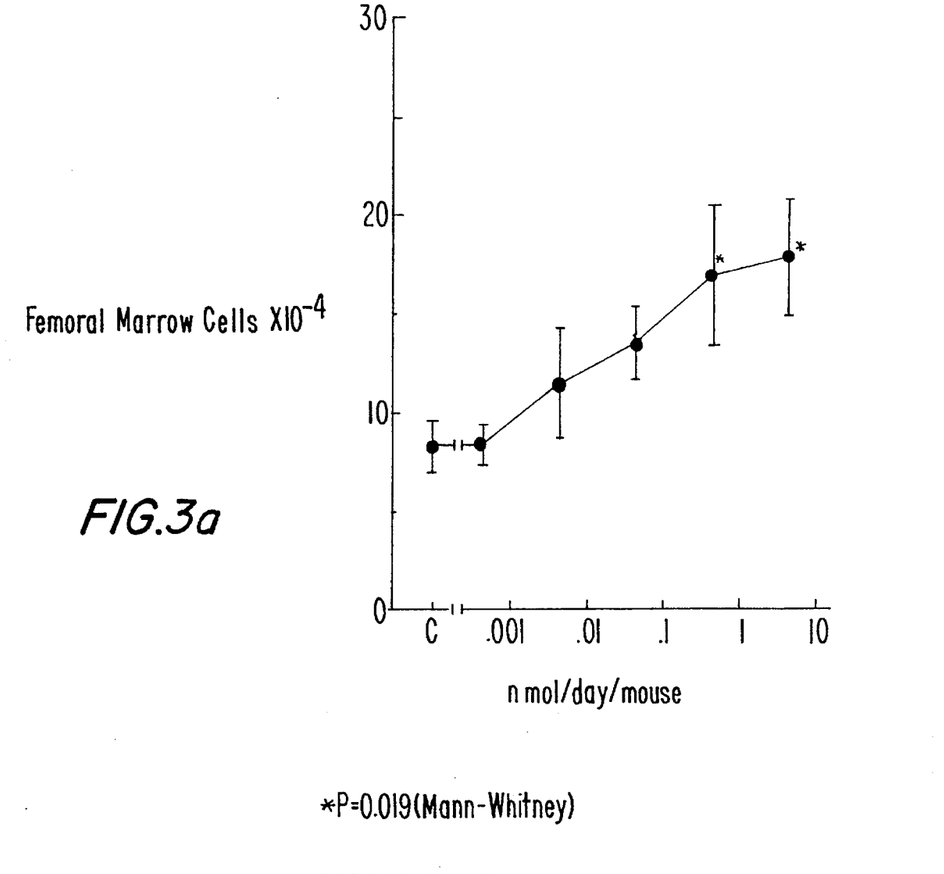
Figure 3B:
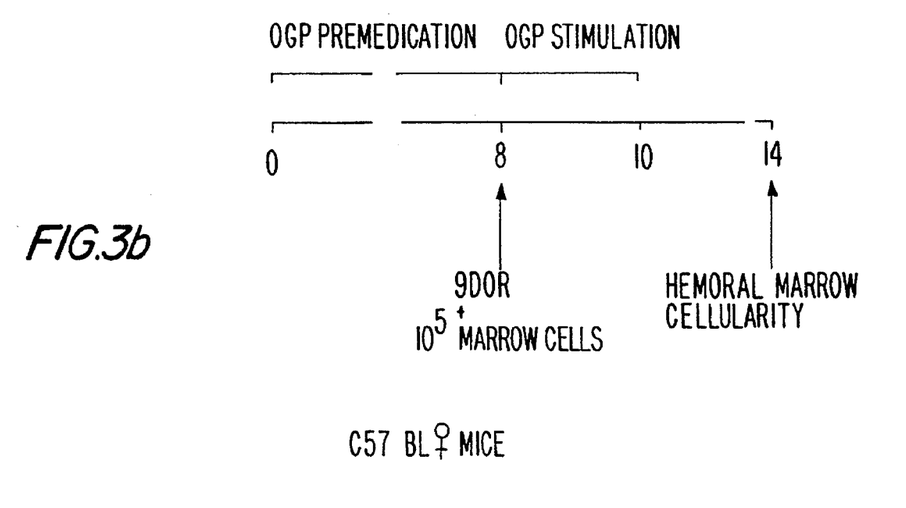

FIG. 3 shows a stimulatory effect of the sOGP on the number of post irradiation/post transplantation femoral bone marrow cells. This effect was characterized by a dose response relationship without any influence at the lowest dose and statistically significant two-fold increase over control of cell counts in mice receiving the two highest doses.

EXAMPLE 6

(PROLIFERATIVE ACTIVITY OF N-TERMINAL TRUNCATED SYNTHETIC OGP ANALOGUES)

MATERIALS

Tissue culture ingredients were purchase from Biological Industries, Beit Haemek, Israel. Culture dishes were from Nunc, Roskilde, Denmark. Bovine serum albumin (BSA), protease inhibitors and N-ethylmaleimide (NEM) were from Sigma Chemical Co., St. Louis, Mo.; Cat. No. A-7030. Centricon-3 microconcentrators were purchased from Amicon, Inc., Beverly, Mass. t-Boc-Gly OCH$_2$-Pam recin, N-Boc protected amino acid derivatives, N,N-dicyclohexylcarbodiimide (DCC), 1-hydroxybenzotriazole (HOBt), diisopropyl-ethylamine (DIEA), trifluoroacetic acid (TFA), N,N-dimethylformamide (DMF) and dichloromethane (DCM) were obtained from Applied Biosytems Inc. (Foster City, Calif.). Hydrogen fluoride (HF) was purchased from Matheson (Secacus, N.J.), Boc-3-I-Tyr(Bzl)-OH from Bachem (Torrance, Calif.), p-Cresol from Aldrich Chemical Co. (Milwaukee, Wis.) and Sephadex G15F from Pharmacia (Uppsala, Sweden). C18 reverse-phase column and acetonitrile were from E. Merck, Darmstadt, Germany. C4 reverse-phase column was from The Separation Group, Hesparia, Calif.

METHODS

Cell cultures

MC3T3 E1 osteoblastic cells or NIH3T3 fibroblasts were maintained in α-Minimal Essential Medium supplemented with 10% fetal calf serum (FCS) and subcultured twice a week. Cells for experiments were derived from maintenance cultures at confluency. For the experiment the cells were seeded in 24 multiwell (2 cm$^2$) tissue culture dishes at $1\times10^4$ cells/cm$^2$. The cultures were incubated at 37° C. in $CO_2$ air. For the initial 46 h the medium was supplemented with 10% FCS and 0.2% nucleosides/ribonucleocides followed by an additional 2 h starvation period under serum free conditions. The different peptides were preincubated with 4% BSA (Sigma Chemical Co., St. Louis, Mo.; Cat. No. A-7030) for 30 min at 37° C., and then added to the cultures. Cell counts were carried out after 48 hours using a hemocytometer.

PEPTIDE SYNTHESIS

Synthetic peptides of this invention were prepared by the solid phase method of Merrifield [Merrifield (1969) Adv. Enzymol. 32:221] using an Applied Biosystems Model 430A Automated Peptide Synthesizer (Applied Biosystems Inc., Foster City, Calif.). The synthesis was carried out on 0.5 mmol t-Boc-Gly-OCH$_2$ resin (1% cross-linked, 0.78 mmol/g). The amino acid derivatives were protected on the α-amino function by t-butyloxycarbonyl (Boc) groups. Protection of the Tyrosine side chain was by 2-Br—Z. The amino acid derivatives were coupled via the DCC-mediated preformed symmetrical anhydride method of Hagemaier, H. and Frank, H. [Hoppe-Seyler's Z., (1972) Physiol. Chem. 353:1973]. The coupling of each amino acid residue was repeated twice. Deprotection of the blocked amino terminus was by treatment with 60% TFA in DCM. Side chains were deprotected and the peptide cleaved from the resin (2.7 g resin-bound peptide) using the HF procedure where a mixture of 4 ml anisole and 36 ml liquid HF was used for 75 min at 0° C. The crude synthetic peptides were partially purified on a Sephadex G15F 3×35 cm column, eluted with 50% (V/V) aqueous acetic acid. Further purification was accomplished on a Waters DeltaPrep 3000 HPLC instrument equipped with a PrePak Vydac protein C18 column (15μ, 5.5×35 cm) (The Separation Group, Hesparia, Calif.). The cartridge was pumped with 5–33.5% acetonitrile linear gradient containing 0.1% TFA at a flow rate of 100 ml/min.

RESULTS

Figure 4A:
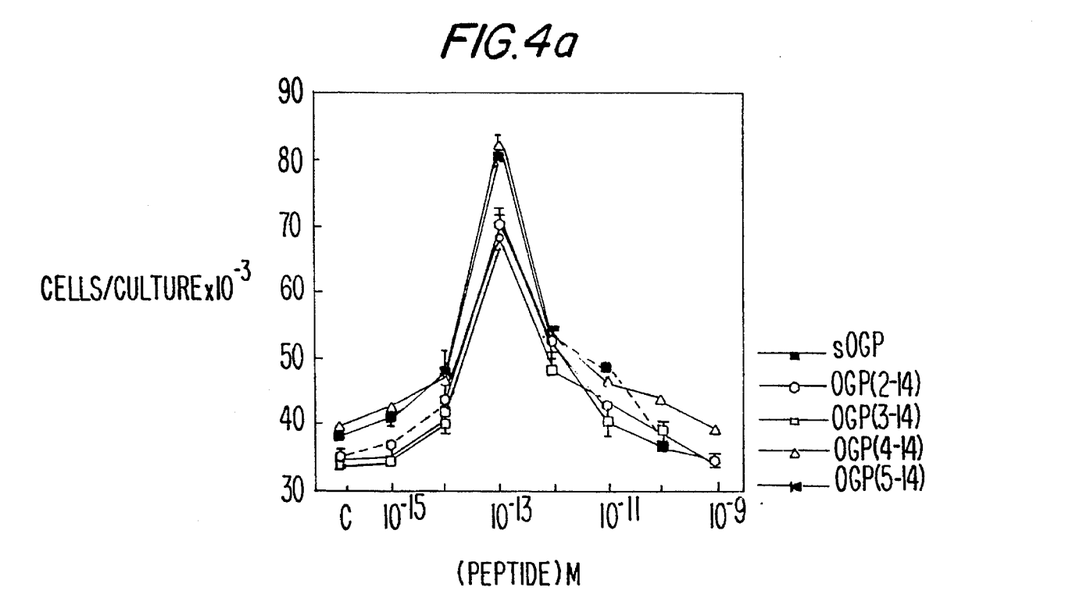
FIG. 4 shows the effect of sOGP, OGP(2–14), OGP(3–14), OGP(4–14) and OGP(5–14) on osteoblastic MC3T3 E1 (A) and fibroblastic NIH 3T3 (B) cell number in vitro. Cell cultures and counts were done as before [Dab et al. (1992) EMBO J. 11:1867]. Data are mean±SEM of triplicate cultures.
Figure 4B:
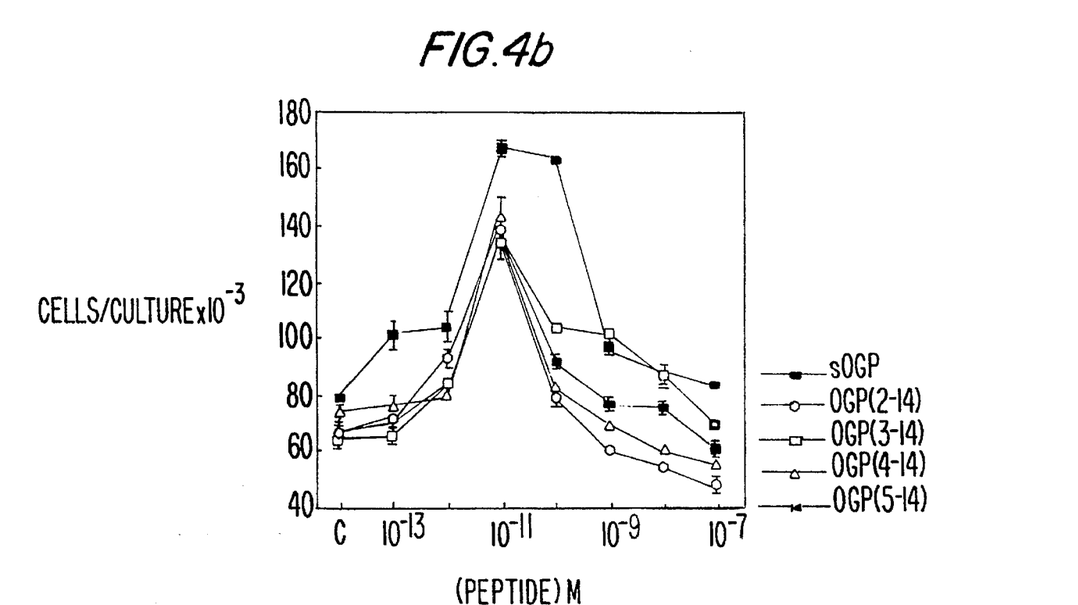

The proliferation effect of either N-terminal truncated synthetic OGP analogues in the MC 3T3 E1 and NIH 3T3 cell assays was similar to that of sOGP positive controls. The respective peak activities were at $10^{-13}$ and $10^{-11}$M peptide concentration (FIG. 4).

What is claimed is:

1. A biochemically pure polypeptide (OGP) having a molecular weight in the range of about 500 to 2600, having a stimulatory effect on osteoblastic cells and in vivo bone formation, and having an amino acid sequence which is at least about 40% conserved in relation to the amino acid sequence Ala-Leu-Lys-Arg-Gln-Gly-Arg-Thr-Leu-Tyr-Gly-Phe-Gly-Gly.

2. A polypeptide according to claim 1 having an amino acid sequence substantially the same as Ala-Leu-Lys-Arg-Gln-Gly-Arg-Thr-Leu-Tyr-Gly-Phe-Gly-Gly.

3. A polypeptide according to claim 1 found in regenerating bone marrow.

4. Osteogenic growth polypeptides which comprise one or more polypeptides each of which have a stimulatory effect on osteoblastic cells and in vivo bone formation and a partial amino acid sequence . . . Ala-Leu-Lys-Arg-Gln-Gly-Arg-Thr-Leu-Tyr-Gly-Phe-Gly-Gly . . . .

5. Osteogenic growth polypeptides which comprise one or more polypeptides each of which have a stimulatory effect on osteoblastic cells and in vivo bone formation and a partial amino acid sequence which is at least about 40% conserved in relation to the amino acid sequence . . . Ala-Leu-Lys-Arg-Gln-Gly-Arg-Thr-Leu-Tyr-Gly-Phe-Gly-Gly . . . .

6. A fragment of the osteogenic growth polypeptides of claim 4 which comprises small peptides with sequences of 6 or more amino acids, said sequences being those of the polypeptides of claim 5.

7. A method for producing an osteogenic growth polypeptide according to claim 1 which comprises isolating said polypeptide from regenerating bone marrow.

8. A method according to claim 7 wherein the polypeptide is free of biochemical debris.

9. A method of increasing bone formation in a mammal which comprises administering to said mammal a therapeutically effective amount of a polypeptide according to claim 1.

10. A method of identifying molecules having a stimulatory effect on osteoblastic cells and in vivo bone formation which comprises:

(a) contacting said molecules with a polypeptide of claim 1; and (b) measuring the effect on osteoblastic cells and in vivo bone formation relative to the effect in the absence of said molecule.

11. A pharmaceutical composition for increasing bone formation which comprises a therapeutically effective amount of a polypeptide according to claim 1 and a pharmaceutically acceptable carrier.

12. A polypeptide according to claim 1 having an amino acid sequence which is at least about 40% conserved in relation to the amino acid sequence Leu-Lys-Arg-Gln-Gly-Arg-Thr-Leu-Tyr-Gly-Phe-Gly-Gly.

13. A polypeptide according to claim 1 having an amino acid sequence which is at least about 40% conserved in relation to the amino acid sequence Lys-Arg-Gln-Gly-Arg-Thr-Leu-Tyr-Gly-Phe-Gly-Gly.

14. A polypeptide according to claim 1 having an amino acid sequence which is at least about 40% conserved in relation to the amino acid sequence Arg-Gln-Gly-Arg-Thr-Leu-Tyr-Gly-Phe-Gly-Gly.

15. A polypeptide according to claim 1 having an amino acid sequence which is at least about 40% conserved in relation to the amino acid sequence Gln-Gly-Arg-Thr-Leu-Tyr-Gly-Phe-Gly-Gly.

16. A method of stimulating hemopoietic reconstruction in a mammal which comprises administering to said mammal a therapeutically effective amount of a polypeptide according to claim 1.

17. A method according to claim 16 for stimulating hemopoietic reconstruction after a bone marrow transplantation in the mammal.

18. A pharmaceutical composition for stimulating hemopoietic reconstruction which comprises a therapeutically effective amount of a polypeptide according to claim 1 and a pharmaceutically acceptable carrier.

19. A pharmaceutical composition according to claim 18 for stimulating hemopoietic reconstruction after a bone marrow transplantation.

* * * * *

UNITED STATES PATENT AND TRADEMARK OFFICE
CERTIFICATE OF CORRECTION

PATENT NO. : 5,461,034

DATED : October 24, 1995

INVENTOR(S) : Bab et al.

It is certified that error appears in the above-identified patent and that said Letters Patent is hereby corrected as shown below:

On the title page item [75],
The names of the inventors should be corrected to read as follows:

ITAI A. BAB, JERUSALEM, ISRAEL; GIDEON A. RODAN, BRYN MAWR, PA; JOHN W. JACOBS, IRVINE, CA; MOHINDER K. SARDANA, LANSDALE, PA; DAN GAZIT, JERUSALEM, ISRAEL; MICHAEL CHOREV, JERUSALEM, ISRAEL; ANDRAS MUHLRAD, JERUSALEM, ISRAEL; ARYE SHTEYER, JERUSALEM, ISRAEL; NURA MANSUR, JERUSALEM, ISRAEL; SHIMON SLAVIN, JERUSALEM, ISRAEL; OLGA GUREVITCH, JERUSALEM, ISRAEL.

Signed and Sealed this

Twenty-third Day of January, 1996

Attest:

BRUCE LEHMAN

*Attesting Officer*   *Commissioner of Patents and Trademarks*